United States Patent [19]
Gorecki et al.

[11] Patent Number: 5,693,071
[45] Date of Patent: Dec. 2, 1997

[54] TAPERED SURGICAL NEEDLES AND SURGICAL INCISION MEMBERS

[75] Inventors: Michael Gorecki, Cromwell; George R. Proto, West Haven; Paul A. Scirica, Huntington, all of Conn.; Stephen W. Zlock, Hawthorne, N.Y.

[73] Assignee: United States Surgical Corporation, Washington, D.C.

[21] Appl. No.: 590,225

[22] Filed: Jan. 23, 1996

[51] Int. Cl.⁶ ............................................. A61B 17/06
[52] U.S. Cl. .................. 606/222; 606/223; 606/224; 66/116; 223/102
[58] Field of Search .................... 606/222–224, 606/225–226; 66/116, 117; 223/102, 103, 104; 289/16; 112/222

[56] References Cited

U.S. PATENT DOCUMENTS

| | | | |
|---|---|---|---|
| 2,516,710 | 7/1950 | Mascolo | 606/223 |
| 4,781,190 | 11/1988 | Lee | 606/139 |
| 5,480,406 | 1/1996 | Nolan et al. | 606/144 |
| 5,569,301 | 10/1996 | Granger et al. | 606/224 |

FOREIGN PATENT DOCUMENTS

| | | | |
|---|---|---|---|
| 540097 | 2/1956 | Italy . | |
| 1253629 | 8/1986 | U.S.S.R. | 606/222 |

*Primary Examiner*—Michael Buiz
*Assistant Examiner*—Tina T. D. Pham

[57] ABSTRACT

A surgical needle is provided including a body portion defining first and second longitudinal ends, the body portion includes a central portion having a first cross-sectional area and end portions adjacent the central portion having a smaller second cross-sectional area. A tissue penetrating portion is provided adjacent at least one end portion. Transition portions are provided intermediate the central portion and the end portions and taper from the first cross-sectional area to the second cross-sectional area. Suture attachment structure is formed in the central portion and a suture is attached to the suture attachment structure. A method of suturing is also provided wherein the surgical needle may be passed through tough tissue while minimizing bending of the surgical needle.

18 Claims, 8 Drawing Sheets

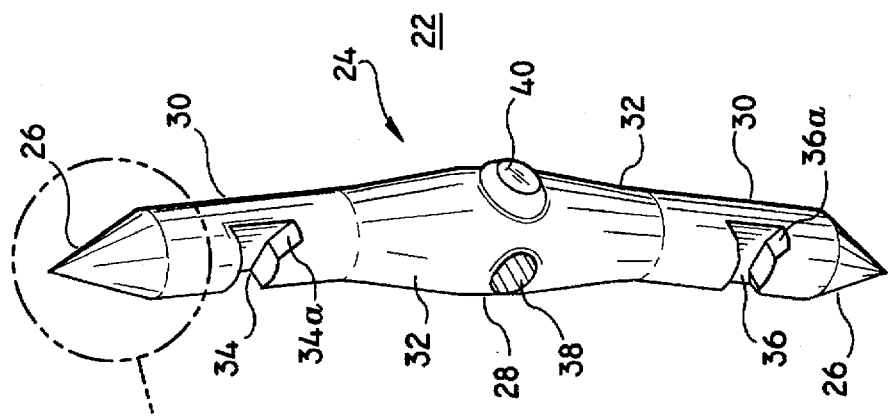
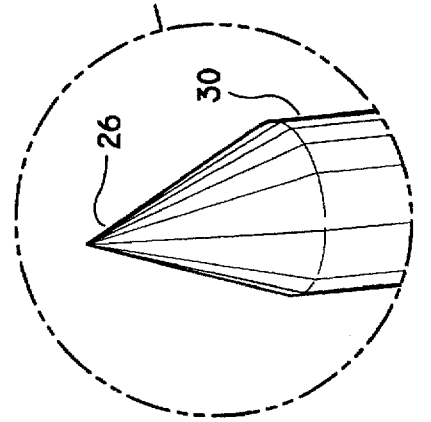
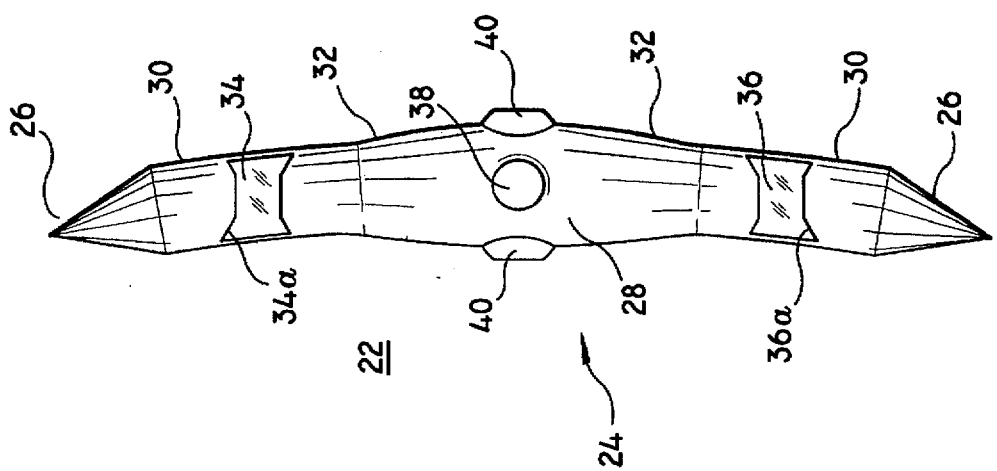

TAPERED SURGICAL NEEDLES AND SURGICAL INCISION MEMBERS

BACKGROUND

1. Technical Field

This disclosure relates generally to surgical suturing instrumentation and, more particularly, to surgical needles and surgical incision members used in conjunction with endoscopic or laparoscopic suturing apparatus.

2. Description of Related Art

Endoscopic or laparoscopic procedures are characterized by the use of an elongated cannula structure having a relatively small diameter with a proximal and distal end. The distal end is passed through the surrounding tissue into a body cavity wherein the surgical procedure or examination is to be effected, thus providing a conduit for the insertion of surgical instrumentation. A plurality of cannula structures may be used to allow insertion of a variety of instruments simultaneously during a given procedure. For example, one cannula may provide a conduit for an endoscope for vision and illumination within the operative cavity, while other cannulas may provide conduits for control of specialized surgical instruments designed for performing specific procedural functions.

Surgical procedures often require placing stitches through tissue, a procedure traditionally accomplished by hand. In endoscopic and laparoscopic surgical procedures, suturing internal body tissue presents a particularly challenging task. In such minimally invasive type surgical procedures, suturing must be accomplished through a cannula port that typically averages between five and ten millimeters in diameter. As used herein, the term "surgical needle" refers to needles having tissue penetrating portions on a least one longitudinal end, while the term "surgical incision member" refers to a particular type of surgical needle having tissue penetrating portions adjacent both longitudinal ends. Surgical incision members are particularly suited for use with surgical suturing instrumentation.

One instrument for facilitating laparoscopic suturing is described in commonly assigned U.S. patent application Ser. No. 08/134,145, filed Oct. 8, 1993, which is incorporated herein by reference. That instrument effects endoscopic suturing by passing a double pointed surgical incision member back and forth through tissue using a unique jaw structure. This jaw structure allows the surgeon to alternately lock the surgical incision member in the first or second jaw. In this manner, tissue can be sutured simply by opening and closing the jaw structure while alternately engaging opposite ends of the surgical incision member.

The shape and design of the surgical incision member is an important aspect of the operation of endoscopic or laparoscopic suturing apparatus. For example, the incision member should be configured to fit down a cannula, preferably transverse to the cannula axis, and easily penetrate tissue when moved in either longitudinal direction with a minimal incision. The surgical incision member should also be capable of drawing an attached suture through the incision with little or no additional trauma to the incision. When operating on tough tissue, such as, for example, Cooper's ligament, such tissue can increase the forces on the surgical incision member. Consequently, the body portion of the surgical incision member should be relatively strong to avoid or minimize bending of the surgical needle as the surgical incision member and suture are pulled through the tough tissue. Further, should bone be encountered, the body portion of the surgical incision member should be strong enough to withstand bending.

SUMMARY

A surgical needle is disclosed having a body portion defining a central portion and first and second longitudinal end portions extending therefrom, at least one tissue penetrating portion positioned adjacent one of the first and second longitudinal end portions and suture attachment structure defined in the body portion. A transition portion is preferably provided intermediate each of the end portions and the central portion. The diameter of the central portion is greater than the diameter of the end portions. The transition portions taper from the diameter of the central portion to the diameters of the end portions. The central portion preferably has a diameter of approximately 0.039 to 0.044 inches. The end portions preferably have a diameter of approximately 0.014 to 0.036 inches. The body portion of the surgical needle preferably has tissue penetrating portions adjacent both the first and second longitudinal end portions to form a surgical incision member.

The body portion preferably is curved and includes first and second apparatus engagement structures for effecting alternate engagement with the jaws of a surgical suturing apparatus. The first and second apparatus engagement structures are preferably recesses formed adjacent the first and second longitudinal end portions of the curved body portion of the surgical needle. The suture attachment structure may include a transverse bore configured to facilitate the attachment of a length of suture therein.

The surgical incision member may further include compression structure which allows the incision member to be crimped or swaged to anchor the suture into the suture attachment structure. In one embodiment at least one protrusion or bulge is positioned on an outer surface of the curved body portion adjacent the transverse bore. The suture is positioned in the bore and the incision member is compressed or swaged so as to force a volume of material into the bore and into contact with the suture therein. Preferably, the at least one protrusion is configured to conform to at least a portion of the circular body. In this configuration, upon compression of the protrusion, material is displaced into the transverse bore while maintaining a substantial uniform cross-section along the body.

A method is also provided for suturing tissue sections while minimizing bending of the surgical needle. The method includes providing a surgical needle having a central portion having a first diameter, end portions having a smaller second diameter, a tissue penetrating portion on at least one of the end portions, and a length of suture affixed to the body portion. A first tissue section is penetrated with the surgical needle. In the event that tough tissue structure or the like is encountered, the larger diameter central portion may be forced through the tissue without bending of the surgical needle. A second tissue section is then penetrated with the surgical needle and the surgical needle is drawn through the first and second tissue sections to draw the length of suture through the first and second tissue sections. The increased diameter of the central portion may increase resistance to bending.

BRIEF DESCRIPTION OF THE DRAWINGS

Various embodiments are described hereinbelow with reference to the drawings, wherein:

FIG. 3 is a side view of one embodiment of a surgical incision member illustrating a body portion having a central portion and end portions having diameters less than that of the central portion and extending therefrom, tissue penetrating portions adjacent either end portion, a suture attachment aperture and crimping bulges, and apparatus engagement structure;

FIG. 4 is a perspective view of the surgical incision member of FIG. 3;

FIG. 5 is an enlarged perspective view of a tissue penetrating portion of the embodiment of FIG. 4;

DETAILED DESCRIPTION OF PREFERRED EMBODIMENTS

Figures 1, 2:
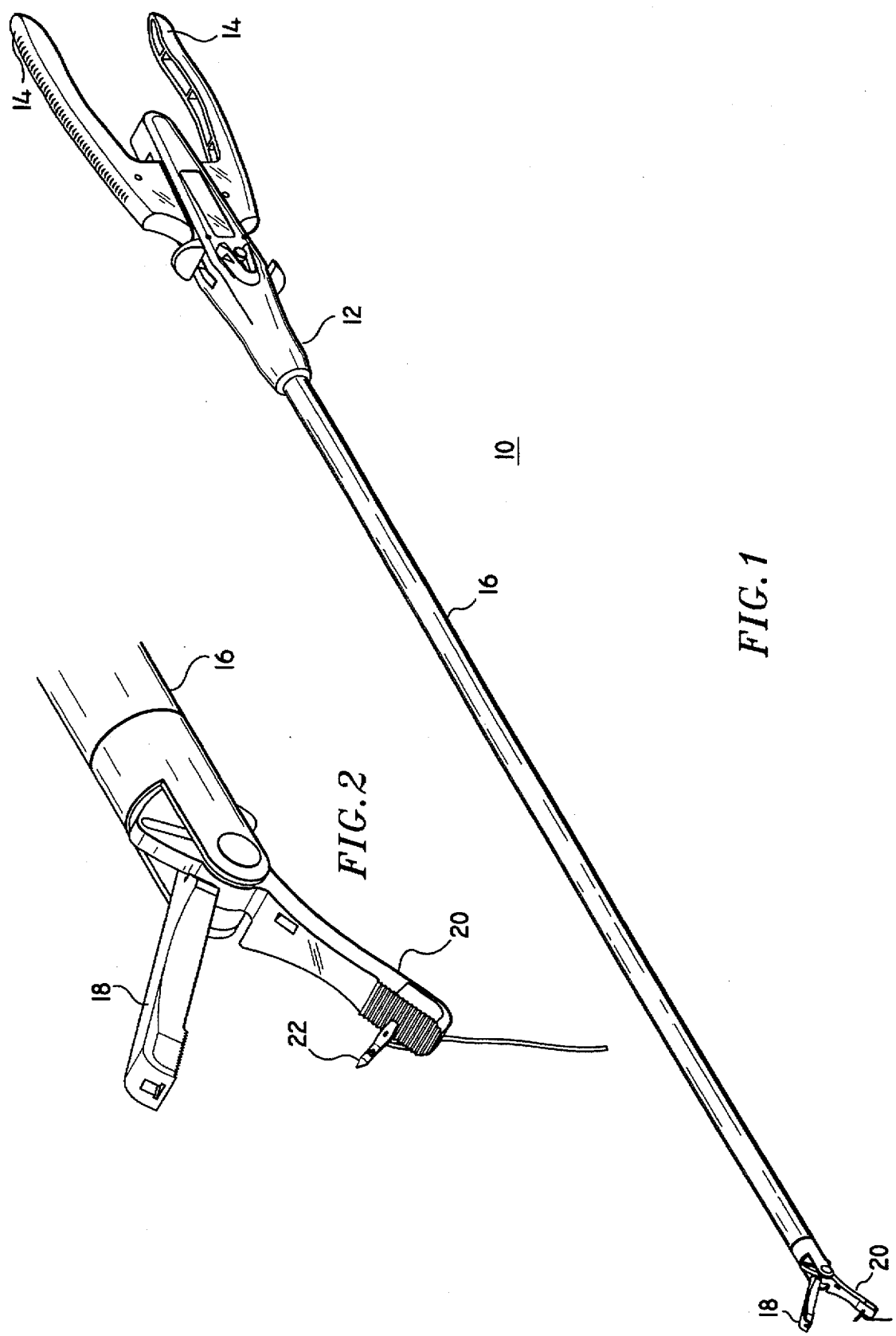
FIG. 1 is a perspective view of an exemplary surgical suturing apparatus incorporating one embodiment of the present surgical incision member.
FIG. 2 is an enlarged view of the distal end of the apparatus of FIG. 1.

Referring now to the drawings and initially to FIGS. 1 and 2, there is shown an exemplary embodiment of a suturing apparatus capable of use in conjunction with various surgical incision member configurations. The suturing apparatus, generally indicated by reference numeral 10, has a handle housing 12 having a two-armed handle 14, an elongated, tubular housing 16 extending from handle housing 12, and upper and lower jaws 18 and 20, respectively, mounted on a distal end of tubular housing 16. Handle 14 is used to control the opening and closing of upper and lower jaws 18 and 20 and is designed to move in the same plane as upper and lower jaws 18 and 20 to provide an ergonomic advantage. Handle housing 12 may also be rotatably connected to tubular housing 16 to provide further ergonomic advantage. This embodiment is particularly well adapted for use in endoscopic or laparoscopic procedures as tubular housing 16 is preferably dimensioned to be deployable through a tubular cannula structure of between about 5 mm to about 10 mm in internal diameter.

Preferred embodiments of novel surgical incision members which may be utilized with the above-described apparatus will now be described. While the following description is directed particularly to surgical incision members, the innovative features disclosed herein are equally applicable to, and contemplated for use with, all types of surgical needles. Referring to FIG. 3, in a preferred embodiment, a surgical incision member 22 includes a body portion 24 having a tissue penetrating portion 26 adjacent each end of body portion 24. Body portion 24 includes a central portion 28 and end portions 30 adjacent each tissue penetrating portion 26. End portions 30 are of a substantially uniform cross-sectional area, circular in cross section, and have a preferred diameter range of approximately 0.034 to 0.036 inches. This particular range of diameters for end portions 30 facilitates the use of surgical incision member 22 in existing surgical suturing apparatus without the need for new or modified jaw structure to accommodate a generally increased diameter of central portion 28 of surgical incision member 22. Preferably, central portion 28 also has a substantially uniform, circular cross-sectional area with a preferred diameter range of approximately 0.037 to 0.044 inches. The increased diameter of central portion 28 over that of end portions 30 significantly increases the bend strength of surgical incision member 22 over that of a surgical incision member formed with a uniform cross-sectional area. In the preferred embodiment, end portions 30 are connected to central portion 28 by transition portions 32. Transition portions 32 are preferably tapered and taper from the larger diameter of central portion 28 to the smaller diameter of end portions 30. The tapers of the transition portions are not limited to straight tapers. Other non-linear tapers are also contemplated.

Body portion 24 of the surgical incision member is preferably arcuate in shape and has a radius of curvature which preferably corresponds to the arc defined by the movement of upper and lower jaws 18 and 20. While central portion 28 and end portions 30 of body portion 24 are preferably circular in cross-section, alternative cross-sectional embodiments are also contemplated. For example, the cross-section of body portion 24 may be oval, square, rectangular, triangular, hollow-ground, or of other non-circular cross-sections. Further, the diameter of end portions 30 may vary slightly from each other while remaining less than the diameter of central portion 28. The surgical incision member may be manufactured using known metal injection molding (MIM) techniques. Alternatively, traditional needle forming techniques may be utilized including extruding, cutting, bending, grinding and polishing wire or other needle stock.

In the embodiment shown in FIGS. 3 and 4, end portions 30 include apparatus engagement structure shown as recesses 34 and 36 which are configured to alternatively engage securing blades of suturing apparatus 10 as described in detail hereinbelow. Recesses 34 and 36 are generally transverse to, and offset from, a center axis of body portion 24. As shown in FIG. 3, recesses 34 and 36 include tapered lead-in portions 34a and 36a, respectively, which facilitate movement of securing blades into each respective recess. Suture attachment structure, in this embodiment shown as aperture 38, is positioned intermediate tissue penetrating portions 26 of surgical incision member 22, and is preferably positioned adjacent the approximate center of central portion 28. Aperture 38 is configured to receive a suture and facilitate securement of the suture to surgical incision member 22, as will be described below. Bulges 40 preferably are provided in body portion 24 adjacent aperture 38 to facilitate securement of the suture therein.

Referring now to FIG. 5, surgical incision member 22 is provided with sharp or pointed tissue penetrating portions 26. Pointed tissue penetrating portions 26 are preferably conical tapering from a maximum diameter, substantially equal to the diameter of end portions 30, to a sharply pointed tip. While the disclosed surgical incision members include relatively sharp or pointed tips, all forms of tissue penetrating tips, including other cutting tips or substantially blunt or radiused tips, are within the scope of the disclosure and are contemplated for use with surgical needles, and in particular, one or both end portions 30 of the surgical incision members. Where the approximate thickness of the tissues to be penetrated is known, over penetration may also be prevented by choosing a surgical incision member having a suitable overall length.

Figure 8:
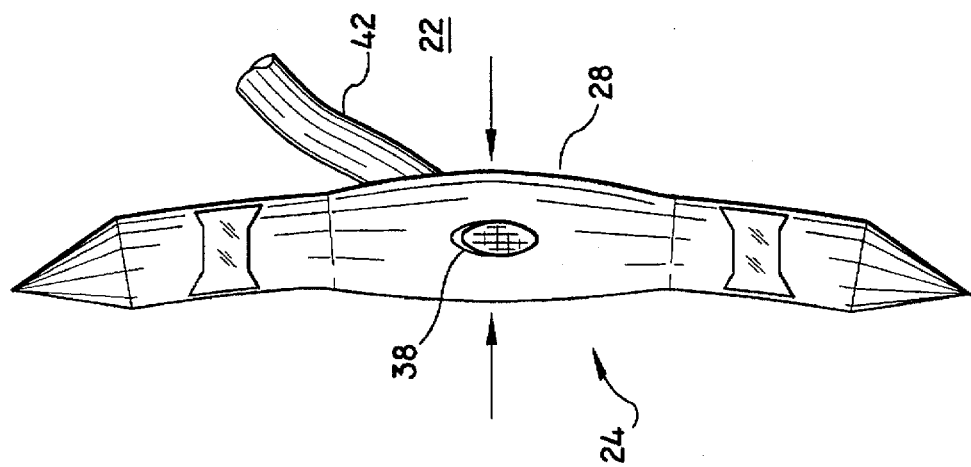
FIG. 8 shows the surgical incision member of FIG. 6 rotated after crimping.
Figure 7:
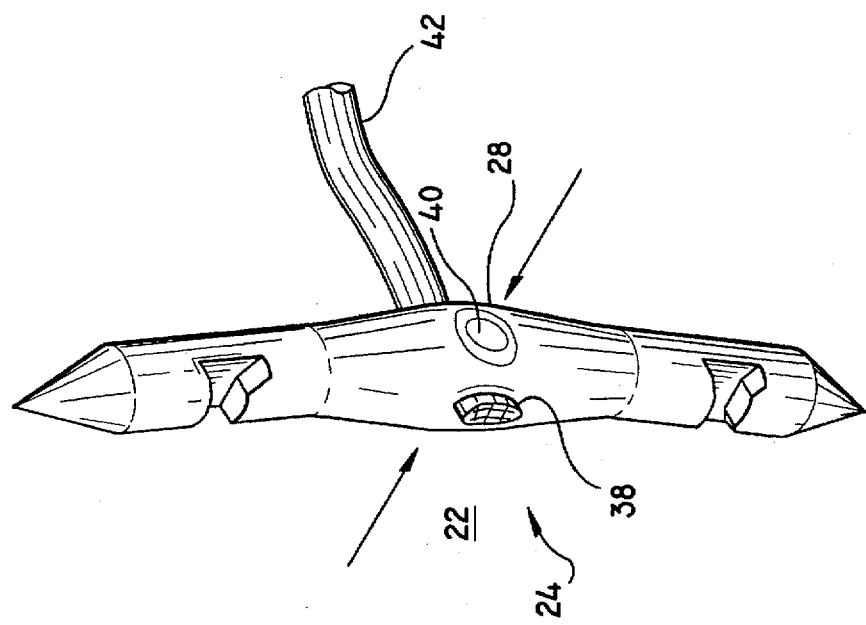
FIG. 7 illustrates the central portion of the surgical incision member of FIG. 6 being crimped onto the suture.
Figure 6:
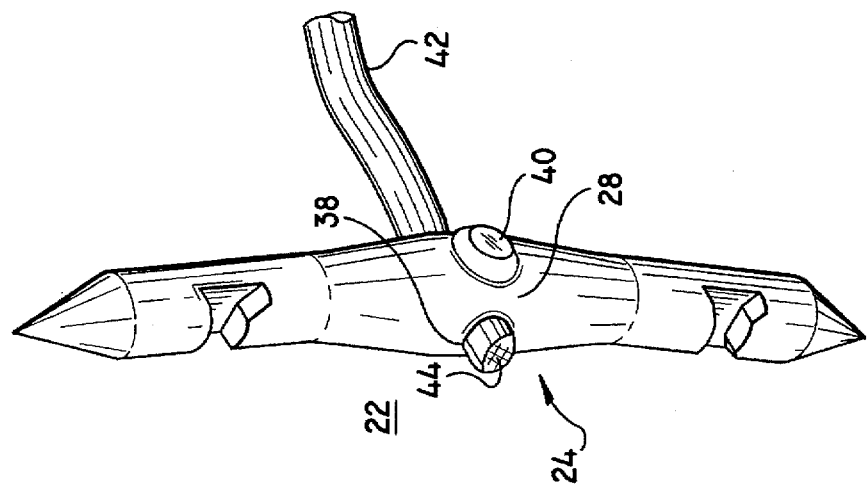
FIG. 6 shows a suture positioned within a bore in the central portion of the surgical incision member of FIG. 4 in preparation for crimping the suture to the surgical incision member.

Referring now to FIGS. 6–8, in order to secure a length of suture 42 within aperture 38 in body portion 24, suture 42 is inserted through suture attachment aperture 38 until a tip portion 44 of suture 42 passes through aperture 38 and suture material occupies aperture 38. Both monofilament and multifilament sutures are contemplated for use with the surgical incision member disclosed herein. Preferably, where a multifilament suture is to be used, one end thereof is tipped to facilitate insertion of the suture into the suture attachment structure. Where monofilament sutures are to be used, no such tipping is required. Where an adhesive is used to secure suture 42 within aperture 38, the adhesive is applied from one or both ends of aperture 38 and wicks into the suture so as to surround the suture and fill suture attachment aperture 38. Suitable adhesives include medical grade cyanoacrylate glue, epoxy cements and other medically acceptable adhesives.

Alternatively, as shown in FIGS. 7 and 8, suture 42 may be attached to surgical incision member 22 by crimping or swaging body portion 24 adjacent suture attachment aperture 38 with one or more dies so as to compress bulges 40 and thus body portion 24 into aperture 38 and crimp the suture into the aperture. Once suture 42 is attached, any excess portion of suture 42 extending through aperture 38 is preferably cut off flush with the surface of body portion 24 to minimize trauma to tissue.

Preferably a pair of dies (not shown) impact bulges 40, to crimp body portion 24 and attach suture 42 thereto by compression force. Preferably, each die has a curved surface with a radius of curvature corresponding to the radius of curvature of body portion 24. Thus, when the dies impact bulges 40, material of body portion 24 is compressed toward the center of aperture 32 and the volume of material of each bulge 40 is displaced inwardly to occupy the portion of body portion 24 which has been deformed to engage suture 42. As a result, when aperture 38 is located through central portion 28 of body portion 24, a substantially uniform cross-section is maintained throughout the length of the central portion 28, including the suture attachment region. Maintaining the uniform circular cross-section along central portion 28 of the surgical incision member minimizes the force required to pass through tissue and also minimizes trauma to the tissue by minimizing the incision size. FIG. 8 illustrates the cross-section of the suture attachment region after the dies have impacted surgical incision member 22.

Figure 9:
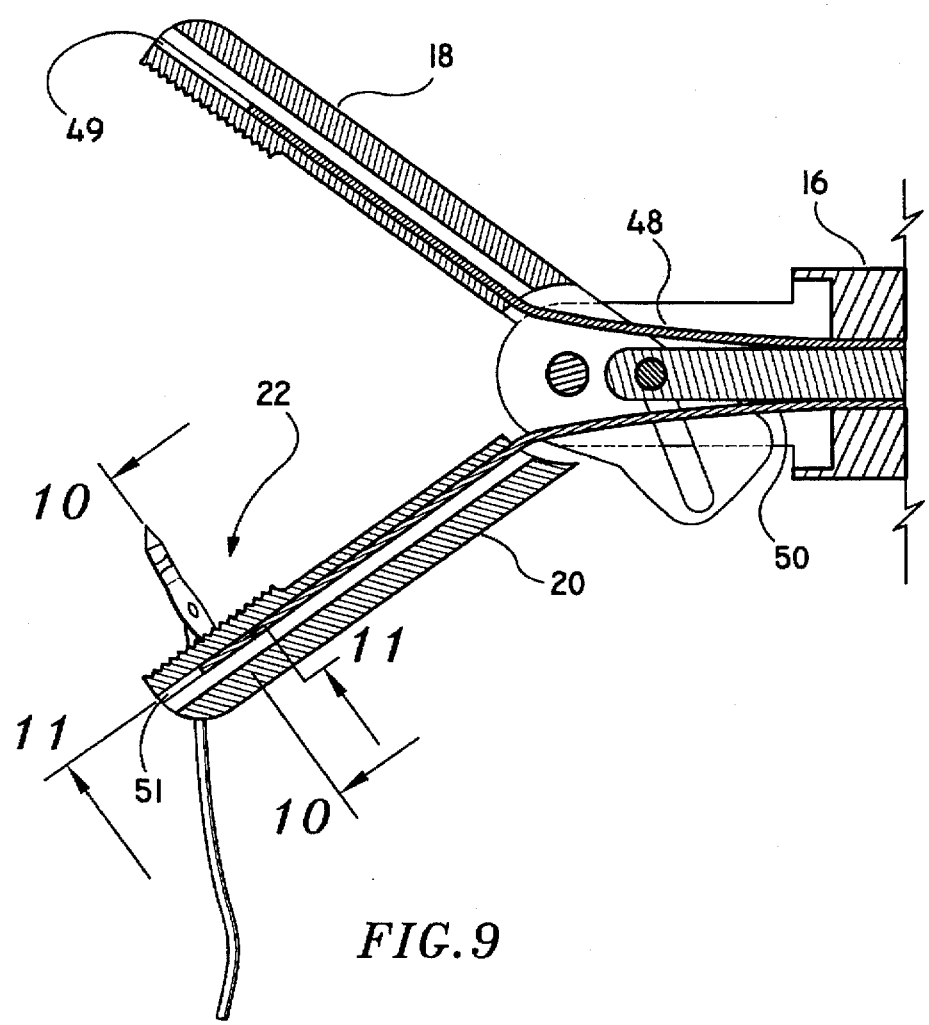
FIG. 9 is a plan view in cross-section of the distal end of the apparatus of FIG. 1, illustrating the jaws in an open position and a surgical incision member secured in the lower jaw.
Figure 10:
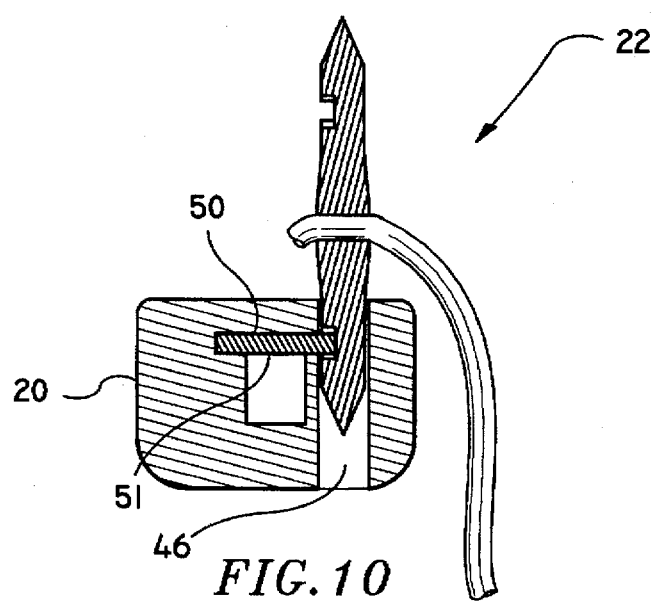
FIG. 10 is a enlarged cross-sectional view taken along the line 10—10 of FIG. 9 and illustrating the blade member securing the surgical incision member within the lower jaw.
Figure 11:
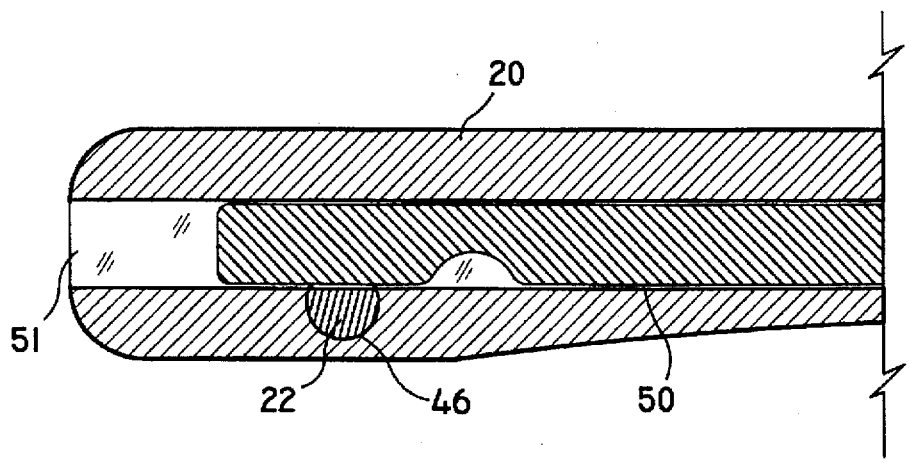
FIG. 11 is a view taken along the line 11—11 of FIG. 9.
Figure 12:
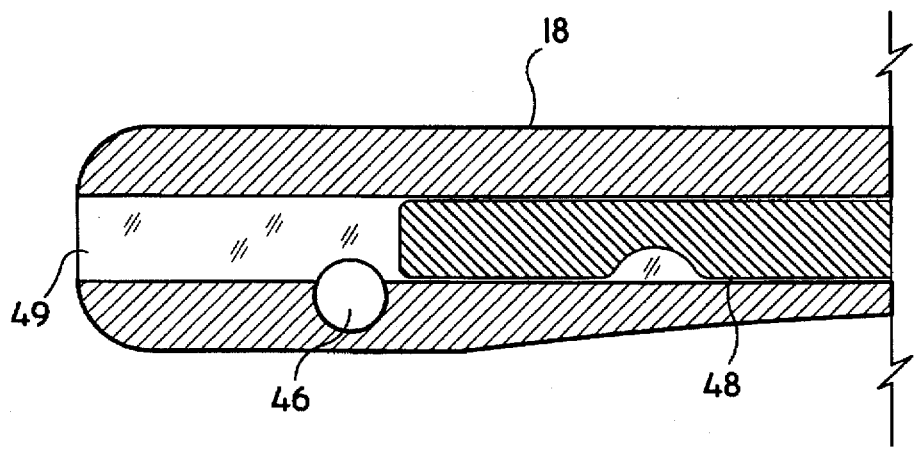
FIG. 12 is a partial cross-sectional view of the upper jaw with a blade member in a disengaged position.

Referring to FIGS. 9 and 10, each of upper and lower jaw 18 and 20, of suturing apparatus 10, is configured to receive a portion of a surgical incision member 22 in recesses 46 (FIG. 10). As noted hereinabove, the diameter of end portions 30 are chosen to be compatible with existing suturing apparatus 10. When upper and lower jaws 18 and 20 are closed, surgical incision member 22 sits in recesses 46 in the jaws. When the jaws are opened, surgical incision member 22 is retained in one of the jaw recesses 46 by a securing blade which intersects recess 36 of surgical incision member 22 through recess 46. As shown in FIGS. 9–12, blade 50, for example, cooperating with lower jaw 20 has been extended through a channel 51 in lower jaw 20 and into recess 46 to secure surgical incision member 22 thereto. Alternatively, blade 48 may extend through a channel 49 in upper jaw 18 and intersect surgical incision member 22 through recess 46, thus securing surgical incision member 22 in upper jaw 18. The movement of the blades to engage surgical incision member 22 is described in more detail in the aforementioned U.S. application Ser. No. 08/134,145.

Figure 13:
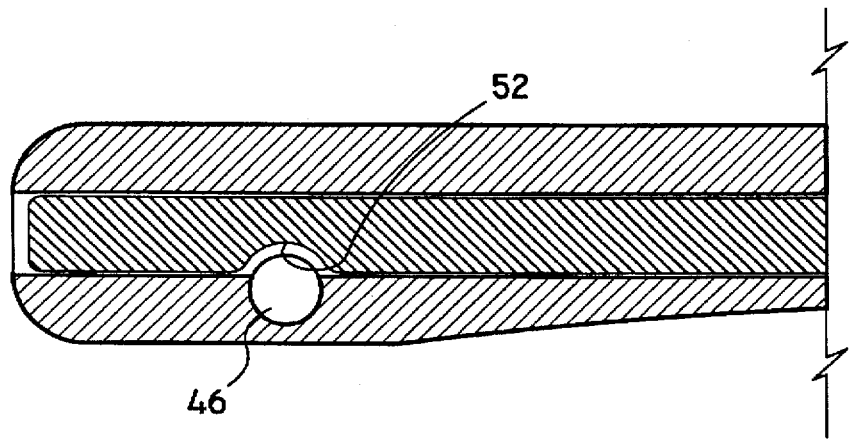
FIG. 13 is a partial cross-sectional view of one of the jaws with a blade member in a loading position.

FIG. 13 illustrates a loading gap 52 provided in at least one of blades 48 or 50 which, when aligned with recess 46, facilitates loading of surgical incision member 22 within a jaw of apparatus 10.

Figure 14:
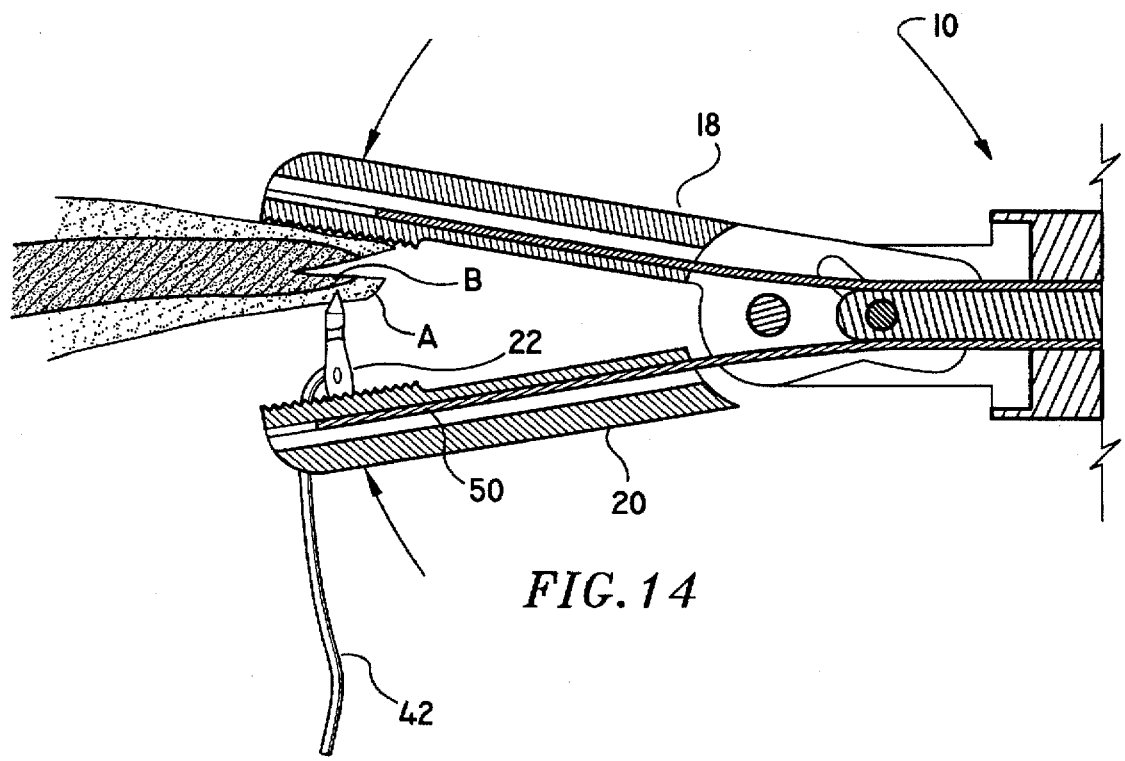
FIG. 14 is a side view, in partial cross-section, of a suturing apparatus loaded with a surgical incision member in a lower jaw and positioned against tissue to be sutured, the surgical incision member being passed through the first tissue section by the suturing apparatus and encountering tougher underlying tissue.

Referring to FIGS. 14–17, in conjunction with FIGS. 1 and 2, in order to operate suturing apparatus 10, jaws 18 and 20 mounting a surgical incision member 22 are opened and positioned around the tissue to be sutured. As shown in FIG. 14, surgical incision member 22 is initially secured to lower jaw 20 by blade 50. Handles 14 are approximated toward each other, closing upper and lower jaws 18 and 20 around the tissue so that the surgical incision member 22 penetrates a first tissue section A. When suturing in the vicinity of tough tissue and the like, for example, tough tissue section B, extra force may be necessary to penetrate tough tissue section B thereby putting a greater lead on central portion 28 of surgical incision member 22. Should this occur, surgical incision member 22 may withstand bending from the greater force due to the increased diameter of central portion 28. Additionally, should bone or body structures be encountered, the increased diameter of central portion 28 aids in withstanding bending.

Figure 15:
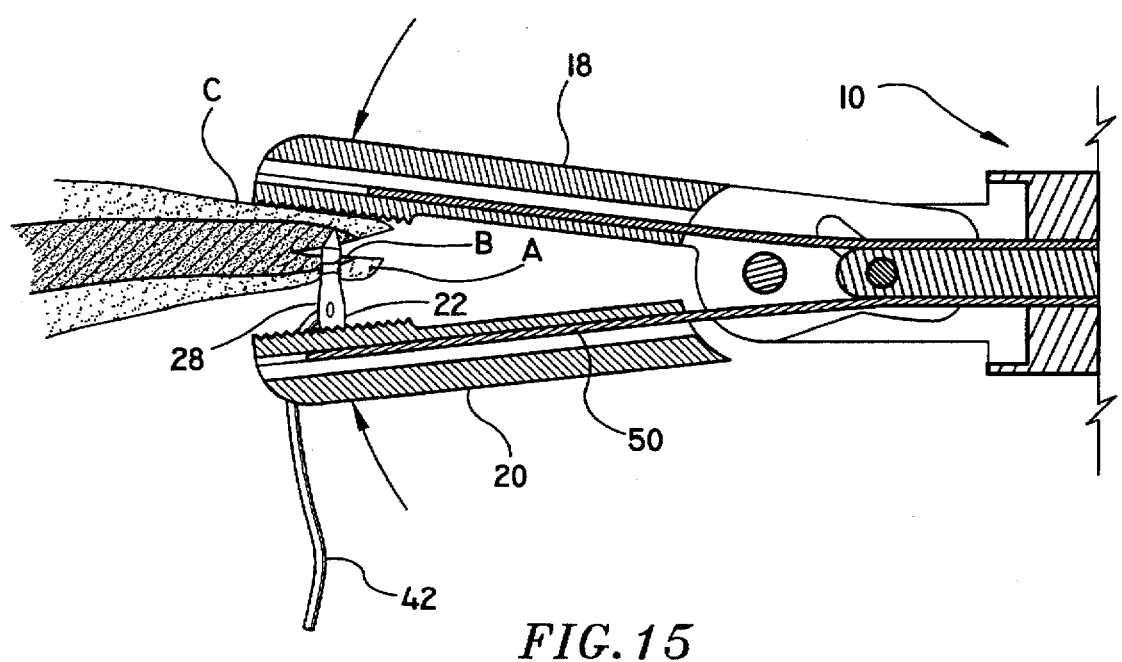
FIG. 15 shows the surgical incision member being forced through the first tissue section, the tougher underlying tissue and a second tissue section by closure of the jaws.
Figure 16:
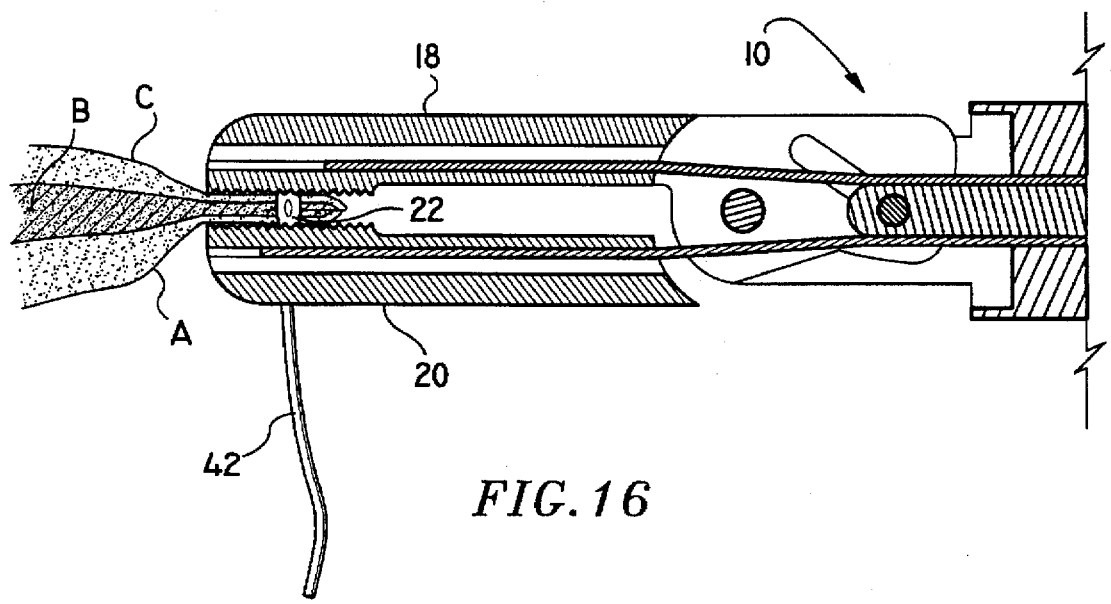
FIG. 16 shows the jaws in a fully closed position after penetrating both the first and second tissue sections and the tougher underlying tissue with the surgical incision member.
Figure 17:
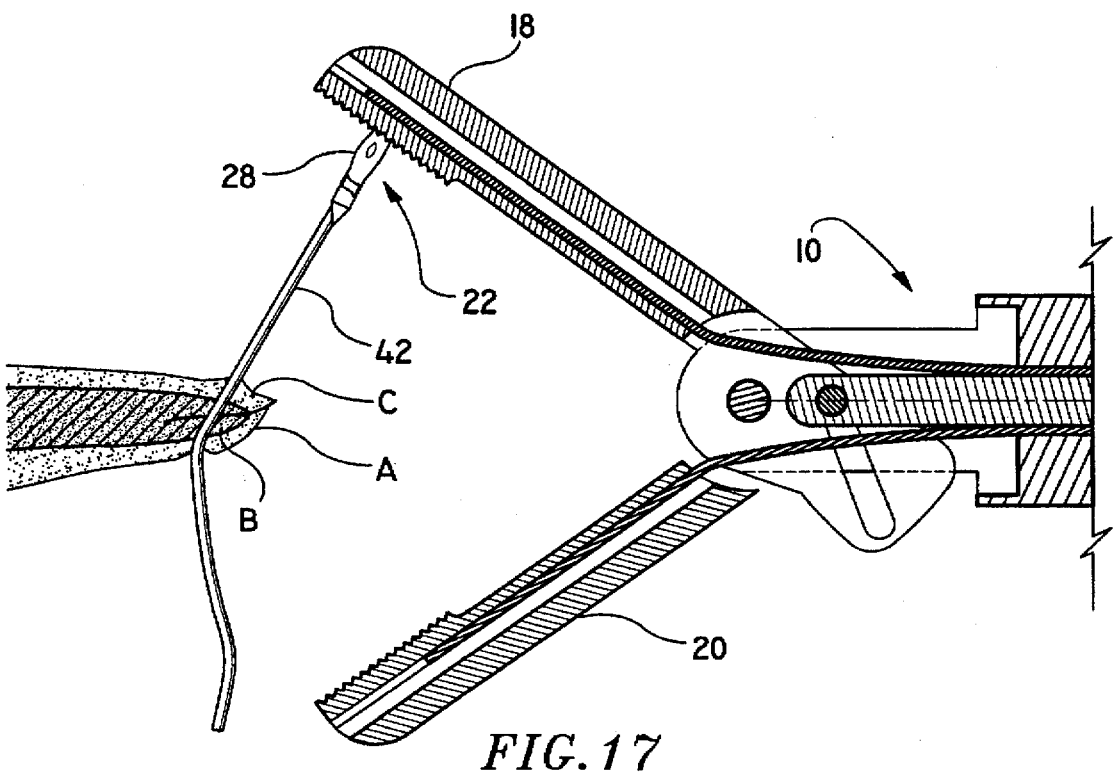
FIG. 17 shows the jaws in an open position and the suture being drawn through the first and second tissue sections and the tougher underlying tissue.

Referring to FIGS. 15 and 16, once surgical incision member 22 has penetrated tough tissue section B, upper and lower jaws 18 and 20 may be fully closed about tissue sections A and B and penetrate second tissue section C. Surgical incision member 22 thus penetrates tissue sections A, B and C and is guided into recess 46 in jaw 18. Once surgical incision member 22 has been secured within recess 46, by alternate movement of blades 48 and 50, the jaws are then opened, as shown in FIG. 17, and suture 42 is pulled through the tissue sections. The surgical incision member is thereby ready to make another stitch by repeating the above described steps.

Figure 18:
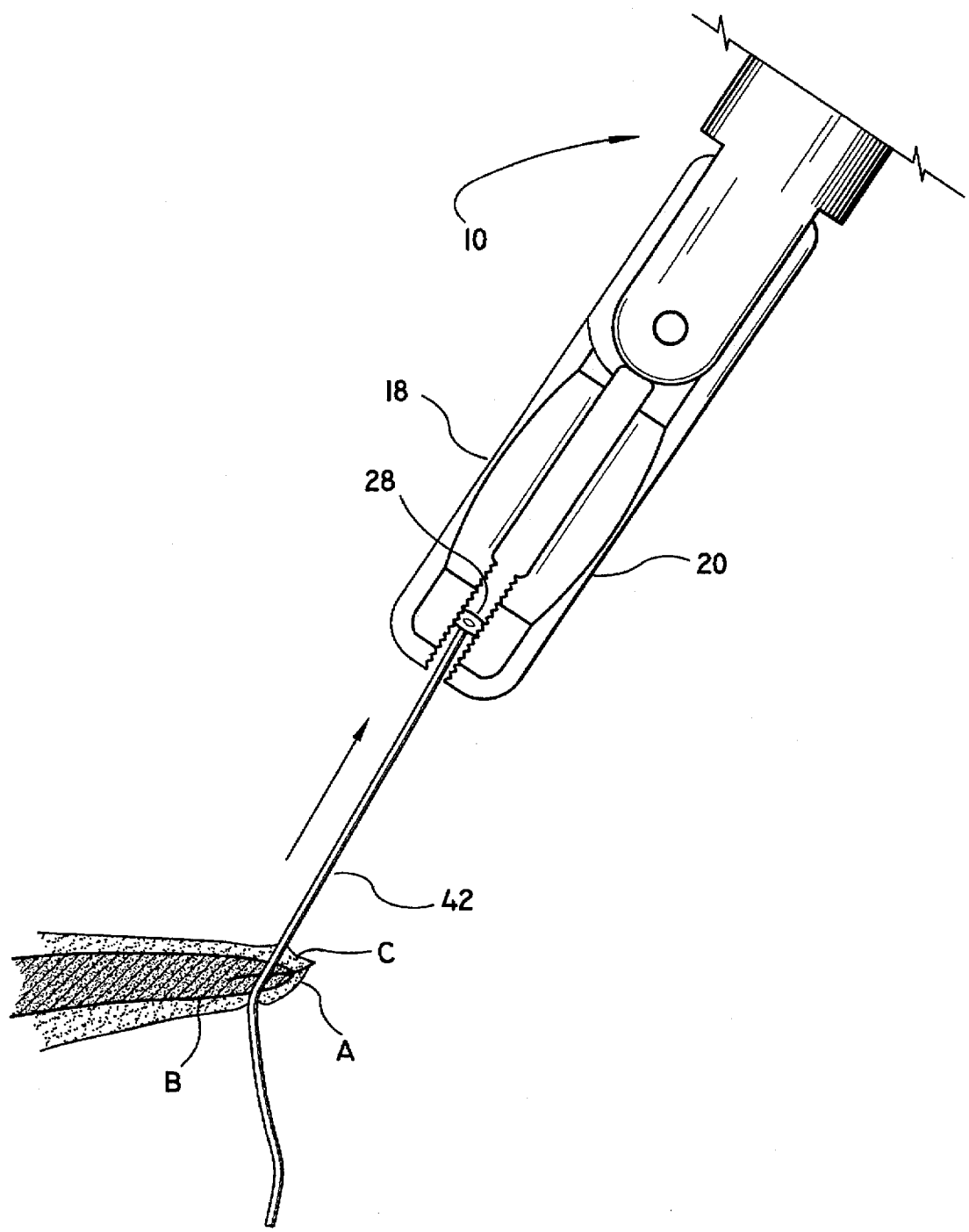
FIG. 18 shows the jaws in a closed position and the suture being drawn through the first and second tissue sections and the tougher underlying tissue.

Referring now to FIG. 18, when drawing suture 42 through very tough tissues, it may be necessary to close jaws 18 and 20 about surgical incision member 22 to support both end portions 30 within recesses 46. The extra drag exerted by the tough tissue B on suture 42 is transmitted to the larger diameter central portion 28. The increased diameter of central portion 28 strengthens surgical incision member 22 thereby avoiding bending of surgical incision member 22 as suture 42 is pulled through the tough tissue.

It will be understood that various modifications can be made to the embodiments disclosed herein. For example, the increased diameter suture retaining central portion is not limited to use only with surgical incision members but may find application in various manner of straight, single pointed or otherwise configured surgical needles. Further, as noted above, various other configurations of the transition portions may be substituted for the relatively straight taper transition portion with similar effect. Additionally, various sizes of the surgical incision members are contemplated, as well as surgical incision members having various types of cross-sections. Apertures as used herein are not limited to through bores and include blind holes. Therefore, the above description should not be construed as limiting, but merely as exemplification of preferred embodiments. Those skilled in the art will envision other modifications within the scope and spirit of the claims appended hereto.

What is claimed is:

1. A surgical needle for remote suturing of tissue comprising:
    a body portion defining a central portion and first and second end portions, the central portion having a first uniform cross-section of a first diameter and the first and second end portions having a second uniform circular cross-section of a second diameter less than the first diameter:
        transition portions intermediate the central portion and the first and second end portions, the transition portions tapering from the first diameter to the second diameter;
        at least one tissue penetrating portion adjacent one of the first and second end portions; and
        suture attachment structure defined in the central portion.

2. A surgical needle as in claim 1, wherein the central portion has a diameter of approximately 0.039 to 0.044 inches.

3. A surgical needle as in claim 2, wherein at least one of the first and second end the portions has a diameter of approximately 0.034 to 0.036 inches.

4. A surgical needle as in claim 1, further comprising sharply pointed tissue penetrating portions adjacent both the first and second end portions.

5. A surgical needle as in claim 1, wherein the suture attachment structure comprises an aperture formed in the central portion.

6. A surgical needle as in claim 5, wherein a suture is fixed in the aperture.

7. A surgical needle for remote suturing of tissue comprising:
    a body portion defining a central portion and first and second end portions, the central portion having a first cross-sectional area and the first and second end portions having a second constant cross-sectional area along the entire lengths thereof, the second cross-sectional area being less than the first cross-sectional area;
    at least one tissue penetrating portion adjacent one of the first and second end portions; and
    suture attachment structure defined in the body portion, the suture attachment structure comprising an aperture formed in the body portion, wherein the body portion includes at least one bulge extending from an outer surface thereof adjacent the suture attachment aperture.

8. A surgical needle as in claim 7, wherein the body portion is substantially circular in cross-section and the at least one bulge is configured to conform to at least a portion of the body portion, such that upon compression of the at least one bulge the body is displaced into the suture attachment aperture and the bulge occupies the displaced portion of the body portion so as to maintain a substantial uniform cross-section along the at least a portion of the body portion.

9. A surgical needle for remote suturing of tissue comprising:
    a body portion defining a central portion and first and second end portions, the central portion having a first diameter and the first and second end portions having a constant second diameter along the entire lengths thereof, the second diameter being less than the first diameter;
    at least one tissue penetrating portion adjacent one of the first and second end portions;
    suture attachment structure defined in the body portion; and
    apparatus engagement structure formed in the body portion, wherein the apparatus engagement structure comprises a substantially transverse recess offset from a center axis of the body portion.

10. The surgical needle as in claim 9, wherein the apparatus engagement structure is formed in at least one of the first and second end portions.

11. A surgical needle for remote suturing of tissue using a surgical apparatus having pivotal jaw structure whose movement defines a predetermined radius of curvature when moved between an open and closed position the surgical needle comprising:
    a curved body portion having a central portion and first and second end portions and defining a predetermined radius of curvature corresponding to the radius of curvature defined by the jaws of the surgical apparatus, the central portion having a first diameter the first and second end and portions having a constant second diameter along the entire lengths thereof, the second diameter being smaller than the first diameter;
    a transition portion intermediate each of the first and second end portions and the central portion, the transition portion tapering from the first diameter to the second diameter;
    a tissue penetrating portion adjacent each of the first and second portions;
    suture attachment structure defined in the central portion for affixing a suture therein; and
    a suture affixed in the suture attachment structure.

12. A surgical needle as in claim 11, wherein the central portion has a diameter of approximately 0.039 to 0.044 inches.

13. A surgical needle as in claim 12, wherein the first and second portions have a diameter of approximately 0.034 to 0.036 inches.

14. A surgical needle as in claim 12, further comprising apparatus engagement structure formed in the body portion.

15. A method of suturing tissue with minimal bending of a surgical needle comprising the steps of:
    a) providing a surgical needle having a central portion with a uniform cross-section of a first diameter, at least one end portion having a uniform cross-section of a second smaller diameter, a tissue penetrating portion formed on the at least one end portion, a transition portion connecting the central portion and the at least one end portion and tapering from the first diameter to the second smaller diameter and a length of suture affixed to the surgical needle;
    b) grasping the surgical needle about the at least one end portion;
    c) penetrating a first tissue section with the surgical needle;

d) penetrating a second tissue section with the surgical needle; and e) drawing the surgical needle through the first and second tissue sections to draw the length of suture through the first and second tissue sections, wherein bending of the surgical needle is minimized by distributing the tension exerted by the tissue sections on the length of suture along the central portion.

16. The method as in claim 15, further comprising the step of securing the surgical needle within a first jaw of a surgical suturing apparatus prior to penetrating the first tissue section.

17. The method as in claim 16, wherein the steps of penetrating the first and second tissue sections include the steps of:

a) positioning the first jaw and a second jaw of the surgical suturing apparatus about the first and second tissue sections; and b) closing the first and second jaws toward each other to force the surgical needle through the first and second tissue sections.

18. The method as in claim 17, wherein the step of drawing the surgical needle through the first and second tissue sections includes the step of:

a) securing the surgical needle within the second jaw and releasing the surgical needle from the first jaw; and b) opening the first and second jaws to draw the surgical needle through the first and second tissue sections.

* * * * *